United States Patent [19]

Donmichael

[11] Patent Number: 4,497,318
[45] Date of Patent: Feb. 5, 1985

[54] ESOPHAGEAL OBTURATOR AIRWAY

[76] Inventor: T. A. Donmichael, 2108/2110 Trustun Ave., Bakersfield, Calif. 93301

[21] Appl. No.: 366,913

[22] Filed: Apr. 9, 1982

[51] Int. Cl.³ .............................................. A61M 16/00
[52] U.S. Cl. .......................... 128/202.28; 128/207.15
[58] Field of Search ...................... 128/202.28, 203.11, 128/207.14, 207.15, 207.16, 206.21, 206.22, 206.23, 206.24, 206.28, 206.29, 207.12

[56]  References Cited
U.S. PATENT DOCUMENTS

| 2,625,155 | 1/1953 | Engelder | 128/206.24 |
| 3,948,255 | 4/1976 | Davidson | 128/202.28 |
| 4,231,365 | 11/1980 | Scarberry | 128/207.15 |
| 4,334,534 | 6/1982 | Ozaki | 128/207.15 |

Primary Examiner—Henry J. Recla
Attorney, Agent, or Firm—Spensley, Horn, Jubas & Lubitz

[57]  ABSTRACT

An esophageal obturator airway divided into an upper section and a lower section with the upper section including apertures for ventilating the lungs and the lower section including a vent tube for venting any stomach fluids.

8 Claims, 3 Drawing Figures

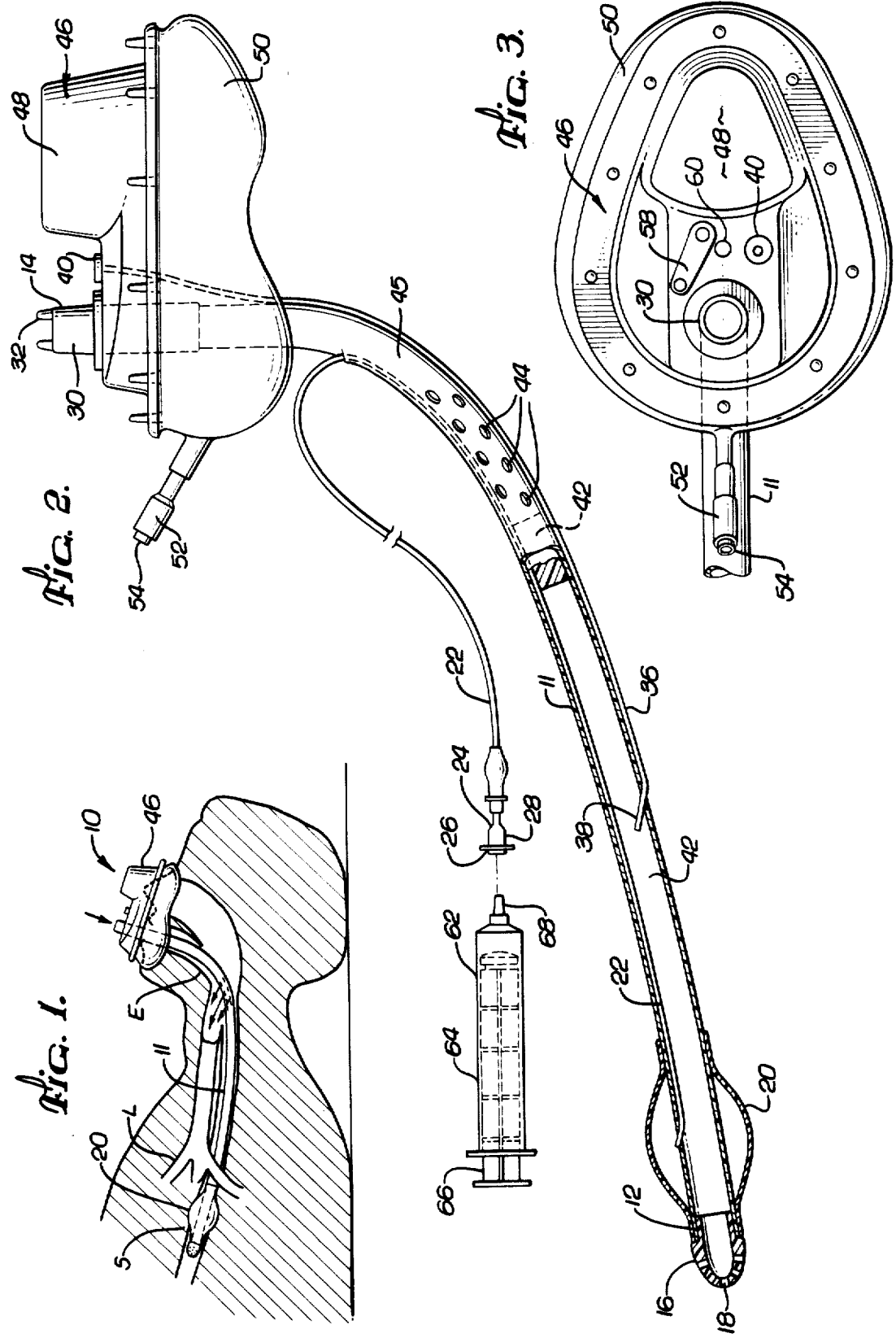

ESOPHAGEAL OBTURATOR AIRWAY

BACKGROUND OF THE INVENTION

1. Field of the Invention

This invention relates to the field of medical devices, and more specifically with artificial respiration or resuscitation devices.

2. Prior Art

Mouth-to-mouth resuscitation is a relatively old technique which has been used on many occasions to save lifes. Such mouth-to-mouth resuscitation has been used as part of the techniques used during cardiopulmonary resuscitation (CPR). One problem with using the mouth-to-mouth techniques as CPR is that, to some, it is unpleasant to place one's mouth directly over someone else's. There is also the problem that as part of the effort, air can inflate the stomach rather than the lungs. This poses a serious risk in that if the stomach contents are aspirated through the esophagus into the mouth and throat passages, there can be gastric spillage into the respiratory passages. If this occurs, the CPR technique may result in failure.

One alternative method available, is to insert an endotracheal tube into the patient to be treated by CPR. Usually, this requires a trained individual usually in a hospital setting. Obviously, where CPR is being used for persons who have drowned, are asphysiated, or have sudden heart arrest, such technique has significant shortcomings.

Recently, a number of devices have evolved which have addressed this problem. See e.g. U.S. Pat. Nos. 3,905,361; 3,841,319 and 3,683,908. While these devices do provide a solution to the problem, they too contain a number of shortcomings. Referring to the device set forth in U.S. Pat. No. 3,905,361, such device, while providing for the problem associated with evacuation of the stomach, ventilates a patient's lungs by introducing air or oxygen into a mask that covers the nose and mouth, and forms a seal against the face. From here, the air flows directly into the lungs without the aid of any duct or other special passage. U.S. Pat. Nos. 3,841,319 and 3,683,908 are directed to devices which provide for means of ventilating a patient's lungs directly through a tube. However, these references solve the problem of respiration of the stomach contents in a manner totally unlike that associated with the present invention. In addition, the face mask associated with the present invention is completely unlike the one shown in the '319 or '908 last two references.

The present invention addresses the shortcomings associated with the prior art devices, and provides a solution which is straight forward. Further, the present invention is easy to use and does not require a hospital setting.

SUMMARY OF THE INVENTION

The esophageal obturator airway (EOA) has been used since in or around 1972 and its role in emergency airway management has recently been accessed. See "The Esophageal Obturator Airway", A Critique by T. A. Don Michael, MD, Journal of the American Medical Association, Sept. 4, 1981, Volume 264. While the efficacy of the EOA and ease of insertion have not been in question, the isolation of the distal third of the esophagus by an inclusive balloon and the potential for trauma to this area on account of gastric contraction has raised some concern. In addition, the possibility of tracheal soiling from secretions pooling in the upper part of the esophagus above the inflated balloon and instances where secretions are copious have also raised concern. Such prior EOA device comprises a tube which is approximately 34 centimeters long, made of semirigid plastic, 13 millimeters in diameter and hollow to the end. Between the upper and middle one-third of the tube are 16 holes. Proximal to the end of the tube is a balloon that preferably lies 22.5 to 26 centimeters from the incisors and below the level of the tracheal bifurcation when the device is properly placed.

A tube lying along the length of the plastic conduit connects the balloon to an inflatable cuff on the face mask. Proximal to the inflatable cuff is a nonreturn valve to which a 35 cc syringe can be attached to inflate the balloon. The proximal end of the plastic tube has a bite block at the level of the incisors and fastens to an orifice in the face mask, which is constructed of clear plastic.

During insertion, the tube tip is lubricated with a water-soluble gel, the balloon is checked for leaks, and the tube is attached to the face mask by a snap lock.

The present device is directed to an improved EOA. These improvements include the following:

1. Gastroesophageal venting

This is accomplished by making an orifice in the distal end of the tube and creating a venting cylinder out of the lower third of the plastic obturator. This lower end, in turn, is vented by a tube which lies alongside the obturator and is led to the outside. The upper end of this cylinder is closed by a silicone plug which reduces dead space and isolates it from the airway. Thus, the plastic tube, which constitutes the major portion of the EOA, is functionally divided into an upper third which functions as an airway and a lower third which functions both as obturator and a gastroesophageal vent.

2. Suctioning of the oropharynx

This is accomplished by a suction flap located on the face mask enabling pharyngeal secretions to be aspirated and tracheal spillage avoided. This is particularly useful in situations of upper pharyngeal bleeding or secretions. The gastroesophageal vent in addition enables the position of the esophageal obturator to be checked and antidotal materials to be administered, if needed. In this manner, the proximal tube conforms to the original devices, while the distal end of the tube enables the stomach and its contents to communicate to the outside. In addition, the suction flap of the mask provides for means of aspiration of upper airway secretion.

The novel features which are believed to be characteristic of the invention, both as to its organization and method of operation, together with further objectives and advantages thereof, will be better understood from the following description considered in connection with the accompanying drawings in which the presently preferred embodiment of the invention is illustrated by way of example. It is to be expressly understood, however, that the drawings are for the purpose of illustration and description only, and are not intended as a definition of the limits of the invention.

BRIEF DESCRIPTION OF THE DRAWINGS

FIG. 1 is a diagrammatic view showing how the device of the present invention is inserted into a patient;

FIG. 2 is a cutaway view showing the main conduit of the present invention; and

FIG. 3 is a front view showing the face mask of the present invention.

Referring first to FIG. 1, the device 10 of the present invention is illustrated as being disposed within the esophagus of a patient and extending into the stomach area. Broadly, the device 10 is comprised of a tube or obturator 11 and a face mask 46. The tube 11 is disposed into the esophagus E and proceeds into the stomach S. As more fully described hereinbelow, when in proper position, a syringe 62 (see FIG. 2) is used to cause balloon 20 to expand such that gastric contents cannot flow from the stomach S into the lungs L.

Referring now to FIG. 2, the tube 11 is shown in greater detail. Tube 11 is made of a nonirritating plastic material which is well known in the art, and has a distal end 12 and a proximal end 14. Adjacent the distal end 12 is a plastic insertion tip 16 which is arranged and configured so as to permit the tube 11 to be inserted into and through the esophagus minimizing trauma to that region. Insertion tip 16 has an axial opening 18 disposed therethrough which is of sufficient diameter so as to permit gastric contends to flow into tube 11. Circumferentially disposed about tube 11 and adjacent the distal end 12 is an expandable balloon 20. As illustrated in FIG. 2, balloon element 20 is in an expanded state and can expand a sufficient amount so as to form a seal isolating the stomach of a patient from the lungs. A conduit or tube 22 runs along the length of tube 11 and is in flow communication with the balloon 20. By flowing fluid, usually air, through conduit 22 into balloon 20, balloon 20 is caused to expand. Tube 22 has a fitting 24 having a port 26 and valve 28 disposed thereon. Fitting 24 is well known in the art and permits fluid to be injected into tube 22. Valve 26 prevents any fluid from escaping. Such one way valves, fittings and ports are well known in the prior art and will not be discussed in any greater detail herein.

Adjacent the proximal end 14 of the tube 11 is a plastic sleeve 30 which has flexible attaching members 32 extending outwardly therefrom. Members 32 have outwardly extending flanges which are used to engage the mask 46 as described in greater detail below.

A second tube or conduit 36 also runs along the length of tube 11. Preferably, a plastic plug or seal 43 is disposed in the tube 11 and divides tube 11 into a first section 42 and a second section 45. Tube 36 is in flow communication with first section 42. More specifically, first port 38 extends into section 42 while second port 40 can be attached to a draining device or the like. Disposed along the length of the second section 45 of tube 11, are a series of openings 44 which permit fluid, such as air, to flow between tube 11 and a patient's lungs.

Referring now to FIGS. 2 and 3, one can see the mask 46 of the present invention. Masks 46 includes a cup shaped section 48 which fits over the patient's nose, and a detachable and deflatable collar 50 which surrounds the mask 46. A fitting 52 which includes a port 54 is joined to the collar 50 and permits the collar to be inflated such that a good seal can be achieved between the mask 46 and the patient's face over the patient's nose and mouth. A flap 58 is provided which selectively covers opening 60. Opening 60 is provided in the mask 46 so as to permit the mask 46 to be selectively opened and pharyngeal secretions which may go into the mouth area suctioned away. This is particularly important in the situation of upper pharyngeal bleeding or secretions. In this manner, tracheal spillage is also avoided. The suction flap 58 also provides a means of precluding aspirations of upper airway secretions.

The operation of the device 10 of the present invention will now be described.

In a typical situation, tube 11 is joined to the mask 46 and the insertion tip 16 is lubricated with a water-soluble gel. In the preferred embodiment, port 30 on mask 46 is configured so as to engage the poximal end 14 of tube 11. Other engagement means, such as slip fittings and the like, are also within the scope of this invention. The expandable balloon 20 is then checked for leakage. The patient's head is moved into a neutral position, and the left hand is used, inserting the thumb as deeply as possible over the back of the tongue and pulling it while using the finger to lift the jaw away from the posterior pharyngeal wall. The tube 11 is grasped below the mask with the right hand and inserted along the tongue and against the posterior phrayngeal wall. The tube is advanced without force until into proper position. Syringe 62 is then joined to the first tube 22. Syringe 62 is of a well recognized construction having a barrel 64 and plunger 66. The tip 68 of the syringe 62 is inserted into the fitting 24 and the plunger 66 depressed. Inflation of the balloon 20 usually requires less than 35 cc's of air. A nonreturn valve 28 ensures that the air stays within the balloon 20. Air or oxygen is now blown into the esophagael tube 11, while the operator or an assistant listens to the lungs with a stethoscope for breathing sounds and to the stomach to ensure that the tube 11 is properly placed. If breath sounds are not heard, the tube 11 is withdrawn and reinserted, with the head in a position of slightly greater flexion. No force should be used during insertion, and the tube should not be tugged at while it lies in the esophagus. Before its withdrawal, the tip 68 of the syringe 62 is used to deflate the balloon 20 fully. The outside of the balloon 20 should be fully flaccid before the tube 11 is withdrawn. No resistance should be encountered. The tube 11 is withdrawn only if a gag reflex is present or an endotracheal tube with an inflated cuff has been implaced.

Although this invention has been disclosed and described with reference to particular embodiments, the principals involved are susceptible of other applications which will be apparent to persons skilled in the art. This invention, therefore, is not intended to be limited to the particular embodiments herein disclosed.

We claim:

1. A medical device for use during cardiopulmonary resuscitation and similar medical procedures, comprising:

(a) a flexible, elongated conduit configured for insertion into the esophagus and having a cross-sectional area approximately the same as the cross-sectional area of a normal esophagus, a proximal end and a distal end, said conduit further having an expandable element joined to said conduit adjacent said distal end, means for expanding said expandable element thereby forming a seal isolating the stomach of a patient from the lungs, a solid sealing plug disposed in said conduit and dividing said conduit into first and second sections, with said first section, having a length approximately twice the length of said second section, adjacent said distal end, said sealing plug preventing fluid from flowing thereacross, a tube means, having a diameter substantially smaller than said conduit, for venting said first section, said tube means being externally joined to and having one end extending from the proximal end of said conduit along the length of said second section and a second end extending through the wall of said conduit such that it is in flow communication with said first section, and a series of openings disposed in said second section and located so as to enable air or other fluid to flow between said second section and the patient's lungs; and (b) a face mask having means for engaging said proximal end of said conduit and said one end of said tube means wherein said engaging means communicates said conduit and said tube means to the exterior of said face mask.

2. A medical device according to claim 1 wherein said distal end of said conduit has an insertion tip defining an opening such that stomach contents can flow through said tip into said first section of said conduit.

3. A medical device according to claim 1 wherein said proximal end of said conduit defines a fluid exchange port, enabling fluid to flow into and be removed from the lungs of a patient.

4. A medical device according to claims 1 or 2 wherein said expandable element is a balloon which circumferentially surrounds said conduit adjacent said distal end.

5. A medical device according to claim 1 wherein said sealing plug defines a solid barrier in said conduit preventing stomach contents from flowing from said first section into said second section.

6. A medical device according to claim 1 wherein said mask further includes an orifice enabling the oropharynx of a patient to be suctioned.

7. A medical device for use during cardiopulmonary resuscitation and similar medical procedures, comprising:

(a) a flexible, elongated conduit configured for insertion into an esophagus and having a cross-sectional area approximately the same as the cross-sectional area of a normal esophagus, a proximal end, and a distal end, said conduit further having an inflatable member joined to said conduit adjacent said distal end, a first tube joined to said conduit for inflating said inflatable member thereby forming a seal isolating the stomach of a patient from the lungs, a solid sealing plug disposed in said conduit and dividing said conduit into first and second sections, with said first section, having a length approximately twice the length of said second section, adjacent said distal end and said second section adjacent said proximal end, said sealing plug defining a barrier which prevents stomach contents from flowing from said first section into said second section, a second tube, having a diameter substantially smaller than said conduit, externally joined to and extending from said proximal end of said conduit along the length of said second section and extending through the wall of said conduit such that it is in flow communication with said first section, said second tube for venting any stomach fluids in said first section, and a series of openings disposed in said second section and located so as to enable air or other fluid to flow between said second section and the patient's lungs; and (b) a face mask having means for engaging said proximal end of said conduit and said one end of said tube means wherein said engaging means communicates said conduit and said tube means to the exterior of said face mask.

8. A medical device according to claim 7 wherein said mask further includes an orifice enabling the oropharynx of a patient to be suctioned.

* * * * *